United States Patent [19]

Löhn

[11] Patent Number: 4,886,455
[45] Date of Patent: Dec. 12, 1989

[54] DENTAL SPRAY HANDPIECE

[75] Inventor: Gerd Löhn, Biberach/Rissegg, Fed. Rep. of Germany

[73] Assignee: Kaltenbach & Voigt GmbH & Co., Biberach an dero Risst, Fed. Rep. of Germany

[21] Appl. No.: 249,725

[22] Filed: Sep. 27, 1988

[30] Foreign Application Priority Data

Oct. 14, 1987 [DE] Fed. Rep. of Germany ....... 3734863

[51] Int. Cl.⁴ ............................................ A61G 17/02
[52] U.S. Cl. ........................................ 433/80; 433/29
[58] Field of Search ................... 433/80, 81, 85, 88, 433/29

[56] References Cited

U.S. PATENT DOCUMENTS

| | | | |
|---|---|---|---|
| 3,109,238 | 11/1963 | Marks | 433/29 |
| 4,619,612 | 10/1986 | Weber et al. | 433/29 |
| 4,629,425 | 12/1986 | Detsch | 433/80 |
| 4,648,838 | 3/1987 | Schlachter | 433/80 |
| 4,711,630 | 12/1987 | Durr | 433/29 |

Primary Examiner—John J. Wilson
Attorney, Agent, or Firm—Scully, Scott, Murphy & Presser

[57] ABSTRACT

A dental spray handpiece, consisting of a gripping sleeve having a media inlet connection at one end thereof and a media discharge at the other end thereof, in which the media conduits are arranged leading from the media inlet connection to the media discharge. A cannula for passing on the media exiting from the media discharge is detachably mounted on the end of the gripping sleeve towards the media discharge, which incorporates passageways for passing on media from the media discharge, and which have outlet orifices discharging into the open at the free end of the cannula, and wherein the spray handpiece further includes a light-emitting element for illuminating the region of the outlet orifices.

6 Claims, 2 Drawing Sheets

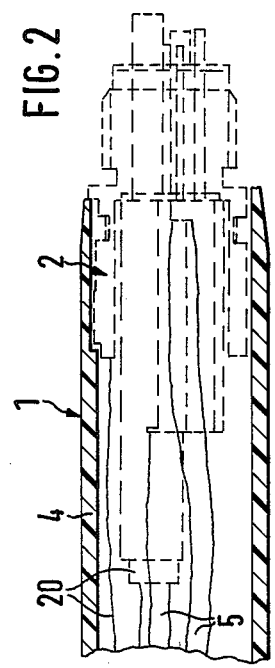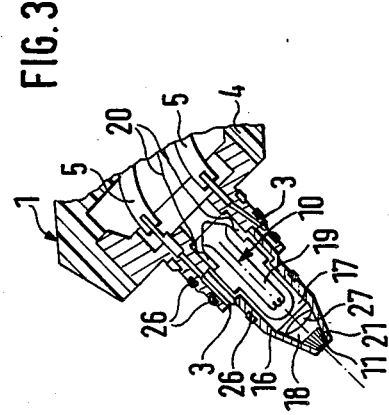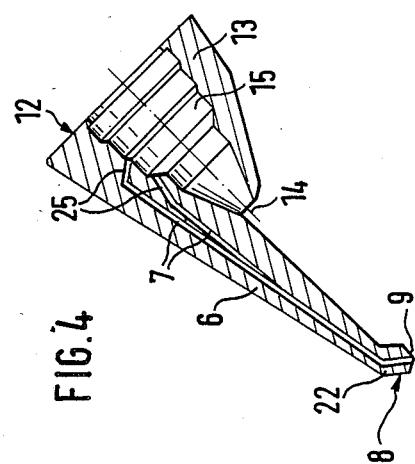

DENTAL SPRAY HANDPIECE

BACKGROUND OF THE INVENTION

1. Field of the Invention

The present invention relates to a dental spray handpiece, consisting of a gripping sleeve having a media inlet connection at one end thereof and a media discharge at the other end thereof, in which the media conduits are arranged leading from the media inlet connection to the media discharge. A cannula for passing on the media exiting from the media discharge is detachably mounted on the end of the gripping sleeve towards the media discharge, which incorporates passageways for passing on media from the media discharge, and which have outlet orifices discharging into the open at the free end of the cannula, and wherein the spray handpiece further includes a light-emitting element or illuminating the region of the outlet orifices.

2. Discussion of the Prior Art

A spray handpiece of that type is known from the disclosure of the German Laid-Open Patent Appln. No. 33 37 166. In this known spray handpiece, the light-emitting element which is constructed in the shape of a light-conductor is arranged within the cannula, whereby the light-conductor, besides the media-advancing passageways, extends to the outlet orifices at the free end of the cannula. This has the result, that the cannula evidences a relatively heavy thickness. Because of the hereby required large cross-sectional dimensions, this obstructs the view of the treating personnel and the handling is rendered more difficult. In addition thereto, because of the only restrictedly sterilizable light-conductor, it is possible to impart only an incomplete hygienic servicing of the cannula which has been detached from the gripping sleeve.

SUMMARY OF THE INVENTION

The present invention provides for a dental spray handpiece of the type described herein which is adapted to obviate or ameliorate the disadvantages encountered in the prior art, in that the light-emitting element is arranged at the end of the gripping sleeve towards the media discharge, and the cannula possesses a light-transmitting aperture which allows for the passage of the light to the region of the outlet orifices. In this instance, the cannula has the smallest possible cross-sectional dimensions and renders possible the hygienic servicing of the cannula.

The advantages which are achieved through the invention can be essentially ascertained in that, due to the omission of the light-emitting element, the cannula forms a slender; in essence, a thin structural component which, especially, in the region of the molars, causes the least possible hindrance to the view of the treating personnel, and facilitates an improved handling. Moreover, the omission of the light-emitting element, that the cannula which is separated from the gripping sleeve and no free of detachable accessories, which is expediently constituted of a unitary material; for example, a plastic material can now be exposed to a satisfactory hygienic servicing or sterilizing.

BRIEF DESCRIPTION OF THE DRAWINGS

Reference my now be had to the following detailed description of advantageous embodiments and features of the invention, taken in conjunction with the accompanying drawings; in which:

FIG. 2 illustrates, on a reduced scale, the end of the spray handpiece of FIG. 1 which is distant from the media discharge;

FIG. 3 illustrates a sectional view of the end of the gripping sleeve for the spray handpiece towards the media discharge, in the absence of the cannula; and FIG. 4 illustrates a sectional view of the cannula shown disassembled from the gripping sleeve.

DETAILED DESCRIPTION

Figure 1:
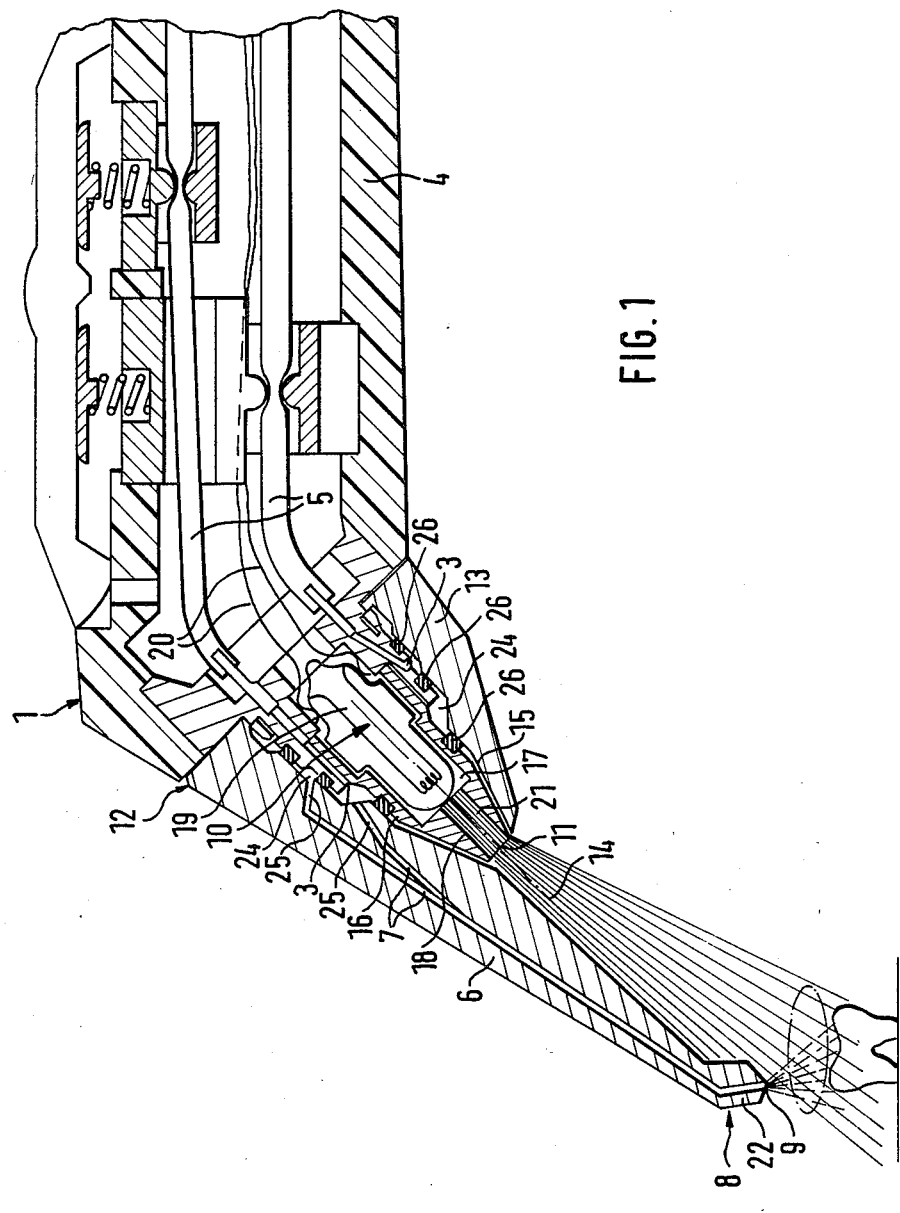
FIG. 1 illustrates longitudinal sectional view of a portion of a spray handpiece towards the media discharge end thereof.

The illustrated dental spray handpiece 1 consists of a gripping sleeve 4 which possesses a media inlet connection 2 at one end thereof and a media discharge 3 at the other end thereof, and in which there are arranged media conduits 5 leading from the media inlet connection 2 to the media discharge 3. A cannula or tubular member 6 is detachably arranged on the end of the gripping sleeve 4 towards the media discharge 3 for further passing on of the media, and which incorporates passageways 7 for passing on the media, which discharge into the open at the free end 8 of the cannula through outlet orifices 9; and wherein the spray handpiece 1 further includes a light-emitting element 10 for illuminating the region of the outlet orifice.

One of the passageways 7 for passing on media can be constituted by a passageway for water, whereas one or two further passageways 7 can be each be constituted of a passageway for air.

The length-emitting element 10 is arranged at the end of the gripping sleeve 4 towards the media discharge, whereby the cannula 6 possesses a light-transmitting aperture 11 which opens up a passage for light to the region of the outlet orifices 9.

An especially suitable embodiment is obtained with regard to the detachable mounting of the cannula 6 on the gripping sleeve 4, as illustrated, the cannula 6 possesses laterally thickened extension 13 at the end 12 which is remote from the free end 8, which is provided with an insert opening 15 with its axis 14 directed towards the region of the outlet orifices 9, for the detachable attachment on a plug connector 16 which projects from the end surface of the gripping sleeve 4 towards the media discharge, which has a hollow space interiorly thereof for the receipt of the light-emitting element 10, and at the end thereof which is distant from the gripping sleeve, includes a light-transmitting aperture 18 for the light emitted by the light-emitting element 10 such that the insert opening 15 is also open for the passage of the light to the free end of the cannula 6.

The cannula 6 is mounted on the plug connector 16 so as to be rotatable about the axis 14 of the insert opening 15.

The light-emitting element 10 can be a light-conductor which is supplied from a light source. With regard to the intensity in the illumination of the region of the outlet orifices 9, it is, however, expedient that as illustrated, the light-emitting element 10 is formed from a lightbulb or incandescent lamp 19, for the operation of which there is provided a current circuit and in the gripping sleeve 4.

The light-conductor 21; for example, a glass insert, is arranged in the light-transmitting aperture 18 of the plug connector 16.

As can be ascertained from FIGS. 1 and 4, the cannula 6 possesses an angled or bent end portion 22 at the end thereof which possesses the outlet orifices 9.

The plug connector 16 which is inserted into the insert opening 15 of the cannula 6, together with the wall structure 23 of the insert opening 15, forms transfer chambers 24 for the transfer of media from the media discharge 3 of the gripping sleeve 4 to radial conduit sections 25 of passageways 7. Hereby, the transfer chambers 24 are sealed by means of seal ring sealing 26 which ar arranged on the plug connector 16. The seal rings 26 are constructed in the shape of 0-rings.

In the embodiment pursuant to FIG. 3, the light-emitting element 10 which is constituted of an incandescent lamp 19 has a front lens 27 attached ahead thereof. This front lens 27 is arranged within the hollow space 17 of the plug connector 16 intermediate the incandescent lamp 19 and the light-transmitting aperture 18 of the plug connector.

The gripping sleeve 4 also possesses respectively a shut off valve 28 for respectively each of the media conduits 5.

The two shutoff valves 28 each possess a push-button 30 which is depressable against the biasing action of a return spring 29 from a closed position into an open position, wherein the two push-buttons 30 are covered by an elastic covering 31.

Instead of being bent or angled as illustrated, the end portion of the gripping sleeve 4 towards the media discharge can also extend straight.

What is claimed is:

1. Dental spray handpiece, consisting of a gripping sleeve having a media inlet connection at one end thereof and a media discharge at another end; a media conduit in said gripping sleeve leading from the media inlet connection to the media discharge; a cannula being detachably mounted at the end of the gripping sleeve towards the media discharge for passing on media discharged from the media discharge, said cannula having passageways for passing on of the media, including outlet orifices at the free end of the cannula for discharging into the open; and a light-emitting element in said handpiece for illuminating the region of the outlet orifices, said light-emitting element being arranged at the media-discharging end of the gripping sleeve, said cannula including a light-transmitting aperture for the passage of light towards the region of the outlet orifices, said cannula incorporating a lateral thickened extension at the end opposite said free end, said extension having an insert opening with an axis directed towards the region of the outlet apertures for the detachable mounting of a plug extension projecting from the end surface of the gripping sleeve towards the media discharge, said thickened extension having an interior hollow space for the receipt of said light-emitting element, and a light-transmitting aperture for the light-emitted by the light-emitting element at the end distant from the gripping sleeve.

2. Spray handpiece as claimed in claim 1, wherein said cannula is mounted on the plug connector so as to be rotatable about the axis of the insert opening.

3. Spray handpiece as claimed in claim 1, wherein a light-conductor is arranged in the light-transmitting aperture of the plug connector.

4. Spray handpiece as claimed in claim 1, wherein said cannula has an angled end portion at the free end thereof possessing the outlet orifices.

5. Spray handpiece as claimed in claim 1, wherein said plug connector inserted into the insert opening of the cannula forms transfer chambers with the wall of the insert opening for the transfer of media transfer from the media discharge of the gripping sleeve to radial conduit portions of the passageways.

6. Spray handpiece as claimed in claim 5, wherein said transfer chambers are sealed by seal rings arranged on the plug connector.

* * * * *